United States Patent [19]

Michaelson et al.

[11] Patent Number: 4,486,613

[45] Date of Patent: Dec. 4, 1984

[54] PROCESS FOR HYDROXYLATING OLEFINS USING AN OSMIUM CARBONYL CATALYST

[75] Inventors: Robert C. Michaelson, Waldwick; Richard G. Austin; Donald A. White, both of Ridgewood, all of N.J.

[73] Assignee: Exxon Research & Engineering Co., Florham Park, N.J.

[21] Appl. No.: 420,137

[22] Filed: Sep. 20, 1982

[51] Int. Cl.$^3$ .................. C07C 29/04; C07C 31/18; C07C 31/22; C07C 31/42
[52] U.S. Cl. .................. 568/860; 260/397.2; 549/243; 560/186; 562/587; 568/458; 568/811; 568/821; 568/833; 568/839; 568/847
[58] Field of Search ............. 568/860, 811, 821, 833, 568/839, 847, 458; 560/186; 562/587; 549/243; 260/397.2

[56] References Cited

U.S. PATENT DOCUMENTS

| | | | |
|---|---|---|---|
| 2,773,101 | 12/1956 | Smith et al. | 568/860 |
| 3,317,592 | 5/1967 | MacLean et al. | 568/860 |
| 3,337,635 | 8/1967 | Norton et al. | 568/860 |
| 3,927,168 | 12/1975 | Whitehead et al. | 568/860 |
| 4,314,088 | 2/1982 | Austin et al. | 568/860 |
| 4,390,739 | 6/1983 | Michaelson et al. | 568/860 |
| 4,393,253 | 7/1983 | Michaelson et al. | 568/860 |

Primary Examiner—J. E. Evans
Attorney, Agent, or Firm—R. A. Maggio

[57] ABSTRACT

A process for hydroxylating olefins, such as ethylene or propylene, using an oxidant selected from organic hydroperoxides, $H_2O_2$, and oxygen and a catalyst composition comprising at least one osmium carbonyl catalyst, such as $Os_3(CO)_{12}$, and optionally at least one cocatalyst such as NaI, is disclosed.

15 Claims, No Drawings

PROCESS FOR HYDROXYLATING OLEFINS USING AN OSMIUM CARBONYL CATALYST

BACKGROUND OF THE INVENTION

The present invention relates to processes for hydroxylating olefins in the presence of an osmium carbonyl containing catalyst, and optional co-catalyst.

Processes for the production of glycols such as ethylene glycol, from olefins are well known in the art.

For example, it is well known from the technical literature and patents that olefins can be effectively oxidized to their corresponding diols with a strong oxidizing agent in the presence of catalytic amounts of specific osmium containing compounds, particularly osmium tetroxide.

The patent literature directed to osmium containing hydroxylation catalysts describes various osmium oxides used in homogeneous reaction systems in conjunction with specific oxidants. The primary oxide catalyst employed in these patents is $OsO_4$, a highly volatile (B.P. 130° C.) and toxic substance. Ordinarily, the toxic nature of $OsO_4$ alone, while troublesome to some extent, could be dealt with by reasonably economic precautions. However, the combined properties of high volatility and toxicity (human tolerance is 0.002 mg/m³ of air) render this compound extremely dangerous necessitating large capital expenditures in plant safety equipment and design if one attempts to commercialize a process employing this compound as a catalyst for use in homogeneous reaction systems. It is for this reason that commercialization of $OsO_4$ based plants has infrequently occurred in the past, if at all. If commercialization is attempted, the aforedescribed capital investment in safety equipment must reduce the profit margin on the products made by these processes.

Accordingly, it would be of extreme economic significance if alternative osmium catalysts could be identified which possess the property of low volatility and/or low toxicity (in relation to $OsO_4$), together with processes for using the same to achieve glycol product selectivity and yield comparable to or better than the conventional $OsO_4$ catalyst.

One important step in this direction is described in U.S. patent application Ser. No. 310,217, filed Oct. 9, 1981 of common assignee herein by R. Michaelson and R. Austin. This application discloses the use of various osmium halides and oxyhalides in the presence or absence of a wide variety of co-catalysts including those employed in the present invention.

Commonly assigned U.S. Pat. No. 4,314,088 and a continuation-in-part thereof, namely, U.S. Pat. No. 4,323,093 filed Oct. 9, 1981 by R. Austin and R. Michaelson collectively, disclose the use of various halide containing co-catalysts in conjunction with osmium tetroxide catalyst and organohydroperoxide oxidants to hydroxylate olefins. The halide containing co-catalysts include alkali and alkaline earth metal halides, hydrogen-halides, quaternary hydrocarbyl phosphonium halides, halogens, and transition metal halides.

Commonly assigned U.S. Pat. No. 4,390,739 filed Oct. 9, 1981 by R. Austin and R. Michaelson is directed to the hydroxylation of olefins using oxygen as an oxidant, a catalytically active metal oxide catalyst such as $OsO_4$, and at least one transition metal salt co-catalyst.

Commonly assigned U.S. patent application Ser. No. 399,270 filed July 19, 1982, by R. Austin and R. Michaelson is directed to a process for hydroxylating olefins in the presence of an organohydroperoxide oxidant, as osmium containing catalyst and an organic halogenated hydrocarbon co-catalyst. The use of osmium carbonyls, while being disclosed as a suitable osmium catalyst, is not specifically claimed in conjunction with any of the halogenated hydrocarbon co-catalysts.

Commonly assigned U.S. patent application Ser. No. 394,414 filed July 1, 1982 by Michaelson and Austin, is directed to the use of carboxylate salts as co-catalysts for use in conjunction with osmium oxides as a catalyst and organohydroperoxides as oxidant to hydroxylate olefins.

Commonly assigned U.S. Pat. No. 4,413,151, filed July 14, 1982 by the inventors herein, is directed to a process for hydroxylating olefins in the presence of a supported osmium catalyst (including supported osmium carbonyls) and a co-catalyst such as those described herein. The oxidant can be any of organic hydroperoxides, $H_2O_2$, and oxygen. The use of osmium carbonyls in the absence of a support is not claimed in this application.

The present invention is directed to the use of still another form of osmium compound which can be employed to catalyze the hydroxylation of olefins, namely, osmium carbonyls. Osmium carbonyls represent a safer, e.g., less volatile osmium compound, relative to $OsO_4$, which can be employed for such catalysis.

While none of the prior art which applicants' are aware disclose the use of osmium carbonyls for directly hydroxylating olefins to their corresponding diols, the following patents are discussed to provide a general background of the prior art.

U.S. Pat. No. 2,414,385 discloses the use of hydrogen peroxide and a catalytically active oxide, such as osmium tetroxide, dissolved in an essentially anhydrous non-alkaline, inert, preferably organic, solvent, to convert, by oxidation, unsaturated organic compounds to useful oxygenated products such as glycols, phenols, aldehydes, ketones, quinones and organic acids. The formation of glycols is achieved by conducting the reaction at temperatures of between several degrees below 0° and 21° C. Such low reaction temperatures drastically, and disadvantageously, reduce the reaction rate to commercially unacceptable levels. At temperatures greater than 21° C., the formation of aldehydes, ketones and acids is favored.

U.S. Pat. No. 2,773,101 discloses a method for recovering an osmium containing catalyst such as osmium tetroxide, by converting it to the non-volatile osmium dioxide form, distilling the hydroxylation product, reoxidizing the osmium dioxide to the volatile osmium tetroxide, and then recovering the same by distillation. Suitable oxidizing agents used to oxidize olefins, and re-oxidize the osmium dioxide, include inorganic peroxides such as hydrogen peroxide, sodium peroxide, barium peroxide; organic peroxides, such as t-butyl peroxide or hydroperoxide, benzoyl peroxide; as well as other oxidizing agents such as oxygen, perchlorates, nitric acid, chlorine water and the like. As with other methods of the prior art, the above process yields undesirable by-products (see col. 1, line 55) thus reducing the selectivity of the process.

British Patent Specification No. 1,028,940 is directed to a process for regenerating osmium tetroxide from reduced osmium tetroxide by treatment of the latter with molecular oxygen in an aqueous alkaline solution. More specifically, it is disclosed that when osmium tetroxide is used by itself as an oxidizing agent, or as a catalyst in conjunction with other oxidizing agents, to oxidize hydrocarbons the osmium tetroxide becomes reduced, and in its reduced form is less active than osmium tetroxide itself. Consequently, by conducting the oxidation reaction in the presence of an alkaline medium and supplying oxygen to the medium throughout the process, the osmium tetroxide is maintained in a high state of activity. The oxidation products disclosed include not only ethylene glycol from ethylene but also organic acids from such compounds as vicinal glycols, olefins, ketones and alcohols.

U.S. Pat. No. 4,255,596 is directed to a process for preparing ethylene glycol in a homogeneous single-phase reaction medium using ethylbenzene hydroperoxide as the oxidizing agent dissolved in ethylbenzene and osmium tetroxide as the catalyst. The pH of the reaction medium is maintained at about 14 by the presence of tetraalkyl ammonium hydroxide. A small amount of water can dissolve beneficially in the medium to reduce by-product formation and improve selectivity to the glycol.

U.S. Pat. No. 4,049,724 describes the preparation of glycols from alkenes and from unsaturated alcohols in an aqueous system using osmium tetroxide and specifying stable and water-soluble aliphatic hydroperoxides, such as t-butyl hydroperoxide, while a critical pH of 8 to 12 is maintained by a suitable combination of alkali metal buffering compounds. The preparation of propylene glycol utilizing t-butyl hydroperoxide is exemplified in the patent at a selectivity based on the hydroperoxide of 45%.

Japanese Patent Application No. Sho 54-145604, published Nov. 14, 1979 is directed to a process for hydroxylating olefins in the presence of $OsO_4$, a quaternary ammonium salt such as tetraethyl ammonium bromide, and a peroxide including organoperoxides and $H_2O_2$ as the oxidant.

U.S. Pat. No. 3,335,174 is directed to the use of water hydrolyzable Group Vb, VI-b and VII metal halides and oxyhalides (e.g., $OsCl_3$) as hydroxylation and esterification catalysts in conjunction with aqueous $H_2O_2$ as an oxidant. However, the process for using this catalyst requires the presence of lower aliphatic hydrocarbon acids such as formic, acetic and propionic acid as solvents. Under these conditions the reaction times vary from ½ to 4 hours, but at the shorter reaction times it is disclosed that substantial amounts of epoxide result. The only yield disclosed is obtained in connection with tungsten hexachloride in Example 1. This yield is extremely low, i.e., 22%, and includes both half-acetate and diol. Thus, among the major disadvantages of the process described in this patent are the low selectivities to diol and the corrosiveness of metal halides in the presence of glacial acids such as acetic acid.

See also: U.S. Pat. No. 3,317,592 (discloses production of acids and glycols using oxygen as oxidant, $OsO_4$ as catalyst at pH 8 to 10); U.S. Pat. No. 3,488,394 (discloses hydroxylation of olefins by reacting olefin and hypochlorite in the presence of $OsO_4$); U.S. Pat. No. 3,846,478 (discloses reaction of hypochlorite and olefin in an aqueous medium and in the presence of $OsO_4$ catalyst to hydroxylate the olefin); U.S. Pat. No. 3,928,473 (discloses hydroxylation of olefins to glycols with $O_2$ oxidant, octavalent osmium catalyst (e.g. $OsO_4$), and borates as promoter); U.S. Pat. No. 3,931,342 (discloses a process for recovering glycols from an aqueous solution containing alkali metal borate and osmium compounds (e.g., $OsO_4$)); U.S. Pat. No. 3,953,305 (discloses use of $OsO_4$ catalyst for hydroxylating olefins which is regenerated by oxidizing hexavalent osmium with hexavalent chromium and electro-chemically regenerating hexavalent chromium); U.S. Pat. No. 4,203,926 (discloses ethylbenzene hydroperoxide as oxidant used in two-phase system to hydroxylate olefins in presence of $OsO_4$ and cesium, rubidium and potassium hydroxides); U.S. Pat. No. 4,217,291 (discloses the oxidation of Osmium (III) to (IV) in an ionic complex with oxygen and an alkali metal, ammonium, or tetra (−lower) alkyl ammonium cation to a valency of greater than +5+organohydroperoxides); U.S. Pat. No. 4,229,601 (discloses the use of cesium, rubidium and potassium hydroxides as promoters for $OsO_4$ catalyst and t-butyl hydroperoxide oxidant for hydroxylating olefins); and U.S. Pat. No. 4,280,924 (discloses a process for regenerating perosmate catalyst, e.g., cesium, rubidium and potassium perosmate).

SUMMARY OF THE INVENTION

In accordance with the present invention there is provided a process for hydroxylating olefins which comprises reacting in admixture water, at least one olefinic compound having at least one ethylenic unsaturation, and an oxidant selected from the group consisting of organic hydroperoxide, $H_2O_2$ and oxygen, in the presence of a catalyst composition in a manner and under conditions sufficient to hydroxylate at least one of said ethylenically unsaturated groups, said catalyst composition (a) being capable of catalyzing said hydroxylation reaction and (b) comprising, as initially added to said admixture, at least one unsupported osmium carbonyl compound and optionally at least one co-catalyst.

DESCRIPTION OF PREFERRED EMBODIMENTS

In accordance with the present invention, at least one olefin containing at least one ethylenic unsaturation is reacted with at least one oxidant, and water in the presence of at least one osmium carbonyl containing catalyst, and optionally but preferably at least one co-catalyst, under conditions and in a manner sufficient to hydroxylate at least one of said ethylenically unsaturated groups to its corresponding diol group.

A. Osmium Carbonyl Catalyst

The present invention employs at least one osmium carbonyl compound as a hydroxylation catalyst. The term osmium carbonyl compound is defined herein broadly to also include ionic and neutral complexes of osmium with at least one carbonyl ligand and optionally other ligands such as phosphines, hydride, halide and the like as described hereinafter.

More specifically, suitable osmium carbonyl catalysts include $Os(CO)_5$, $Os_2(CO)_9$, $Os_3(CO)_{12}$, $Os_5(CO)_{16}$, $Os_6(CO)_{18}$, $Os_7(CO)_{21}$, and $Os_8(CO)_{23}$.

Osmium carbonyl complexes suitable for use as the osmium carbonyl catalyst include those represented by the formulae: $[Os(CO)X_5]^{-2}$, $[Os(CO)_2X_4]^{-2}$, $[Os(CO)_3X_3]^{-1}$, $[Os(CO)_4X]^{-2}$, and $Os(X'')_a(CO)_b(Y)_c(PR_3)_d$, wherein X is halogen, preferably iodine, X'' is independently selected from hydrogen (i.e. hydride), cyclopentadienyl (CPD), and halogen (preferably iodine), Y is independently selected from NO, $NH_3$, and $N_2$, R is a hydrocarbyl group independently selected from alkyl, typically alkyl of from about 1 to 10, preferably from about 1 to 5, most preferably from about 1 to 3 carbons, aryl, typically aryl of from about 6 to about 14, preferably from about 6 to about 10, most preferably about 6 carbons, alkaryl and aralkyl wherein the alkyl and aryl groups thereof are as defined immediately above, "a" and "c" represent numbers of from 0 to about 3, "b" represents a number of at least 1, "d" represents a number of 2 or 3 and the sum of a, b, c, and d is selected in conjunction with the valence of Os to achieve a neutral complex.

Representative examples of suitable osmium carbonyl complexes include $[Os(CO)Cl_5]^{-2}$, $[Os(CO)I_5]^{-2}$, $[Os(CO)_2Br_4]^{-2}$, $[Os(CO)_2I_4]^{-2}$, $[Os(CO)_3I_3]^{-1}$, $[Os(CO)_3Cl_3]^{-1}$ $[Os(CO)_4I]^{-2}$, $[Os(CO)_4Cl]^{-2}$, Os ($\pi$-CPD)$_2$(CO) (P$\phi_3$)$_2$, OsCl$_2$(CO) (P$\phi_3$)$_2$, Os(CO)$_3$(P$\phi_3$)$_2$, OsHCl(CO) (P$\phi_3$)$_3$, OsI(CO) (NO) (P$\phi_3$)$_2$, OsHCl(CO) (PEt$_2\phi$)$_3$, OsI$_2$(CO) (P$\phi_3$)$_2$, OsHI(CO) (P$\phi_3$)$_3$, and mixtures thereof; "Et" representing ethyl, "$\phi$" representing phenyl, and $\pi$-CPD representing pi-bonded cyclopentadienyl.

The preferred osmium carbonyl catalyst is Os$_3$(CO)$_{12}$.

The aforenoted osmium carbonyl compounds can be prepared by conventional methods as described in "Inorganic Synthesis", Vol. 13, p. 92 (F. A. Cotton ed. 1972); "Quarterly Reviews", Vol. 24, p. 498 (1970); and "Advanced Inorganic Chemistry", Cotton and Wilkinson, p. 1000 to 1017 (3rd. ed. 1972).

The osmium carbonyl compounds are employed in amounts effective to catalyze the hydroxylation reaction. Thus, while any effective amount of catalyst will suffice, it is preferred that such effective amounts constitute typically from about $1 \times 10^{-1}$ to about $1 \times 10^{-8}$ moles, preferably from about $1 \times 10^{-2}$ to about $1 \times 10^{-6}$ moles, and most preferably from about $1 \times 10^{-2}$ to about $1 \times 10^{-5}$ moles, of osmium in the osmium carbonyl catalyst per mole of olefin ethylenic unsaturation to be hydroxylated.

Alternatively, such amounts may be expressed as varying from about 1 to about 10,000, preferably from about 50 to about 1,000, and most preferably from about 200 to about 800 ppm, based on the total weight of liquid reaction medium.

The osmium carbonyl catalysts are soluble in aqueous and/or organic polar solvent systems described hereinafter and can be dissolved in said systems for addition to the reaction mixture.

The aforedescribed osmium carbonyl catalysts can be employed alone or in conjunction with one or more promoters (also referred to herein as co-catalysts) which increase the rate and/or selectivity of the hydroxylation reaction. Such promoters or co-catalysts can be those conventionally employed in conjunction with $OsO_4$ as well as those disclosed in other commonly assigned U.S. patent applications.

For example, suitable promoters or co-catalysts include alkali metal (e.g., Li, Na, K, Rb, Cs, and Fr), and alkaline earth metal (e.g., Be, Mg, Ca, Sr, Ba and Ra): halides, hydroxides and/or oxides, carboxylates, aryloates, aryolates and pseudo halides; tetra hydrocarbyl ammonium: hydroxides, halides, carboxylates, aryloates, and aryolates; tetra hydrocarbyl phosphonium: hydroxides, halides, carboxylates, aryloates, aryolates; transition metal: halides, porphyrins, carboxylates, and aryloates; hydrogen halides; halogenated hydrocarbons such as alkyl, aryl, aralkyl, alkaryl and cycloalkyl halides; Group III-b (i.e., B, Al, Ga, In, Tl), IV-b (i.e., Si, Ge, Sn, Pb), V-b (i.e., N, P, As, Sb, Bi) and VI-b (i.e., S, Se, Te, Po) halides, and the halogens $F_2$, $Cl_2$, $Br_2$.

More specifically, suitable alkali and alkaline earth metal halide co-catalysts (referred to herein as Group 1 co-catalysts) include the Li, Na, K, Rb, and Cs iodides, bromides, chlorides and fluorides; and Mg, Ca, Sr, and Ba, iodides, bromides, chlorides, and fluorides and mixtures thereof. Preferred Group 1 co-catalysts include the Na, K, Rb, Cs, Mg and Ca halides.

Suitable alkali and alkaline earth metal hydroxide co-catalysts (referred to herein as Group 2 co-catalysts) include LiOH, NaOH, KOH, RbOH, CsOH, Ca(OH)$_2$, Ba(OH)$_2$, Mg(OH)$_2$ the corresponding oxides thereof, and mixtures of the same.

Preferred Group 2 co-catalysts include the Na, K, Rb, Mg and Ca hydroxides.

Suitable alkali and alkaline earth metal: carboxylate aryloate, and aryolate co-catalysts (referred to herein as Group 3 co-catalysts) include those which possess as anions respectively:

(a) carboxylate anions represented by the structural formula:

wherein R$_1$ can be substituted or unsubstituted: alkyl, typically alkyl of from about 1 to about 10 carbons, preferably about 1 to about 5 carbons and most preferably about 1 to about 3 carbons, cycloalkyl, typically cycloalkyl of from about 4 to about 20, preferably from about 5 to about 15, and most preferably from about 6 to about 10 carbons, or aralkyl, typically aralkyl wherein the aryl group thereof is as defined in connection with Ar of structural formula (II) below and the alkyl group thereof is as defined immediately above; said R$_1$ substituents including: hydroxyl; halide (i.e., F, Cl, Br, and I); ether groups represented by the structural formulae —O—R$_2$ and —R$_3$—O—R$_2$ wherein R$_2$ and R$_3$ are independently selected from the group consisting of alkyl, typically about C$_1$ to about C$_{10}$ alkyl, preferably about C$_1$ to about C$_5$ alkyl, and most preferably about C$_1$ to about C$_3$ alkyl; and ester groups represented by the structural formulae:

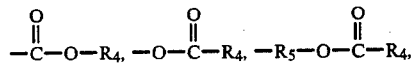

and

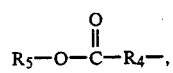

wherein R$_4$ and R$_5$ which may be the same or different are as defined in connection with R$_2$ and R$_3$; and mixtures thereof;

(b) aryloate anions represented by the structural formula:

wherein Ar is selected from the group consisting of substituted and unsubstituted: aryl, typically aryl of from about 6 to about 14 carbons, preferably from about 6 to about 10 carbons, (e.g., 6 carbons), and alkaryl, typically alkaryl wherein the alkyl group is from about 1 to about 6 carbons, preferably from about 1 to about 3 carbons, and the aryl group thereof is as defined above, and wherein said substituents on the Ar group are as defined above in connection with $R_1$; and (c) aryolate anions represented by the structural formula:

$$Ar-O^- \qquad (III)$$

wherein Ar is as described above in connection with structural formula (II), and preferably is aryl.

Illustrative examples of such Group 3 co-catalysts include: sodium acetate, potassium acetate, calcium acetate, cesium acetate, magnesium acetate, sodium propanoate, magnesium butanoate, strontium pentanoate, sodium benzoate, potassium benzoate, magnesium benzoate, calcium benzonate, sodium naphthoate, potassium naphthoate, beryllium naphthoate, sodium 4-(6-methyl-2-naphthyl) pentanoate, potassium 3-(7-methyl-1-naphthyl)-propanoate, magnesium 2-(4-propyl-1-benzyl) ethanoate, calcium phenolate, sodium naphtholate, potassium naphtholate, sodium 3-(ethoxy) propanoate, potassium 4-(propoxy carbonyl) butanoate, calcium 3-(propyl carbonyl oxy) propanoate, magnesium 2-(methyl carbonyl oxy methyl) acetate, beryllium 4-(ethoxy carbonyl methyl) butanoate, cesium 4-(ethoxy methyl) benzoate, sodium 3-(propoxy) naphthoate, potassium 4-(ethoxy carbonyl) benzoate, barium 2-(hydroxy) acetate, rubidium 2-chloropropanoate, magnesium 4-bromobenzoate, magnesium phenolate, and mixtures thereof.

Preferred Group 3 co-catalysts include the Na, K, Rb and Cs acetates.

Suitable alkali and alkaline earth metal pseudo halide co-catalysts (referred to herein as Group 4 co-catalysts) include those which possess pseudo halide anions selected from the group consisting of: $SCN^-$, $SeCN^-$, $TeCN^-$, $OCN^-$, and $CNO^-$, and mixtures thereof.

Illustrative examples of such Group 4 co-catalysts include NaSCN, NaSeCN, KSeCN, CsSeCN, NaTeCN, KTeCN, NaOCN, NaCNO, KOCN, KCNO, CsOCN, CsCNO, CsTeCN, $Mg(SeCN)_2$, $Ca(TeCN)_2$, $Ca(OCN)_2$, $Ca(CNO)_2$.

Preferred Group 4 co-catalysts include the Na, K, Rb and Cs thiocyanates.

Tetra hydrocarbyl ammonium or phosphonium salt co-catalyst (referred to herein as Group 5 co-catalysts) possess a cation and an anion. The respective cations can be represented by the respective structural formula $(R)_4N^+$ and $(R)_4P^+$ wherein R is a hydrocarbyl group independently selected from the group consisting of substituted and unsubstituted: alkyl, typically alkyl having from about 1 to about 30 carbons, preferably from about 1 to about 20 carbons, and most preferably from about 1 to about 10 (e.g. 1-5) carbons, aryl, preferably aryl having from 6 to about 14 carbons, and most preferably from 6 to about 10 carbons, and alkaryl and aralkyl wherein the aryl and alkyl groups thereof are as described immediately above; said R substituents being as defined in connection with the substituents of $R_1$ described above. Accordingly, the term hydrocarbyl is intended to include both substituted and unsubstituted groups, and mixtures thereof. The anion of the Group 5 co-catalysts are selected from the group consisting of hydroxyl, halide, pseudo halide, carboxylate, aryloate and aryolate, said pseudo halide, said carboxylate, aryloate, and aryolate anions, being as defined above in connection with the anions of the alkali and alkali metal salt co-catalysts described above.

Illustrative examples of such Group 5 co-catalysts include tetra methyl ammonium bromide, tetra ethyl phosphonium chloride, tetra decyl phosphonium bromide, tetra phenyl ammonium chloride, tetra phenyl phosphonium bromide, dimethyl diethyl ammonium iodide, methyl triethyl phosphonium chloride, tetra butyl ammonium chloride, phenyl trimethyl ammonium bromide, phenyl trimethyl phosphonium chloride, phenyl triethyl ammonium iodide, phenyl triethyl phosphonium chloride, tetra ethyl ammonium hydroxide, tetra butyl ammonium hydroxide, tetra ethyl phosphonium hydroxide, phenyl triethyl ammonium hydroxide, phenyl trimethyl phosphonium hydroxide, tetra-ethyl ammonium acetate, tetra butyl phosphonium acetate, phenyl triethyl ammonium acetate, phenyl trimethyl phosphonium acetate, tetraethyl ammonium benzoate, phenyl trimethyl phosphonium benzoate, phenyl triethyl ammonium naphthoate, tetra ethyl ammonium phenolate, tetra butyl phosphonium naphtholate, tetra 2-(methoxy) ethyl phosphonium chloride, tetra 4-(propoxy methyl) phenyl ammonium bromide, di 3-(methoxy carbonyl) -propyl -diethyl phosphonium iodide, di 4-(ethyl carbonyloxy) butyl-dimethyl ammonium chloride, tetra 5-(ethoxy carbonyl methyl) pentyl phosphonium bromide, tetra 4-hydroxy butyl ammonium acetate, tetra 3-chloropropyl phosphonium acetate, tetra methyl ammonium thiocyanate, tetra ethyl phosphonium salenio cyanate, tetra (4-methyl phenyl) ammonium chloride, tetra (3-phenyl-1-propyl) phosphonium bromide.

Preferred Group 5 co-catalysts include the unsubstituted tetra lower alkyl (e.g., $C_1$ to $C_5$ alkyl) ammonium hydroxide, iodides, bromides, fluorides, chlorides and acetates.

Transition metal containing co-catalysts (referred to herein as Group 6 co-catalysts) include those having a cation and anion wherein the transition metal cation is selected from the group consisting of cations of Fe, Co, Ni, Cu, V, Cr, Mn, Sc, Ti, Mo, Ru, Rh, Pd, and W, preferably Cu, Fe, Ni, Co and Mn, most preferably Cu, and mixtures thereof.

Anions of the Group 6 co-catalysts include halide, porphyrin (as defined in the Condensed Chemical Dictionary 9th ed. revised by G. Hawley (1977) including benzoporphyrins), pseudo halide, carboxylate and aryloate; said pseudo halide, carboxylate and aryloate anions being as defined generally in connection with the alkali and alkaline earth metal containing co-catalysts and as illustrated by specific examples of suitable anions in conjunction with other co-catalysts described herein.

Representative examples of Group 6 co-catalysts include $FeF_3$, $FeCl_3$, $FeBr_3$, $FeF_2$, $FeCl_2$, $FeBr_2$, $FeI_2$, $CoCl_2$, $CoF_3$, $CoF_2$, $NiF_2$, $NiBr_2$, $NiI_2$, $NiCl_2$, $CuBr_2$, $CuI_2$, $CuF_2$, $CuI$, $CuCl$, $CuBr$, $VF_5$, $VF_4$, $VF_3$, $VF_2$, $VCl_4$, $VCl_3$, $VBr_4$, $VBr_3$, $VI_3$, $CrF_2$, $CrF_3$, $CrF_4$, $CrF_5$, $CrF_6$, $CrCl_3$, $CrCl_4$, $CrBr_3$, $CrBr_4$, $CrI_3$, $MnCl_2$, $MnCl_3$, $MnCl_4$, $MnBr_3$, $MnI_3$, $ScCl_3$, $ScBr_3$, $ScF_3$, $TiCl_4$, $TiBr_4$, $TiF_4$, $MoCl_3$, $Mo_2Cl_{10}$, $MoBr_4$, $Mo_2F_9$, $MoF_6$, $MoF_5$, $RuF_5$, $RuF_3$, $RuF_4$, $RuF_6$, $RuCl_3$, $RuCl_4$, $RuCl_6$, $RuBr_6$, $RhF_3$, $RhF_4$, $RhF_6$, $PdF_2$, $PdCl_2$, $PdBr_2$, $PdI_2$, $WCl_6$, $WBr_5$, $WCl_3$, $WBr_3$, $WI_3$, copper acetate, copper naphthoate, copper benzoate, copper propanoate, iron acetate, iron benzoate, iron naphthoate, copper 4-ethyl benzoate, iron 4-butyl benzoate, nickel acetate, nickel benzoate, nickel naphthoate, copper decanoate, iron hexanoate, iron phthalocyanine, manganese phthalocyanine, copper phthalocyanine, nickel phthalocyanine, and the Fe, Mn, Cu, and Ni porphyrin salts.

Preferred Group 6 co-catalysts include copper bromide, chloride, iodide, and acetate; iron bromide, chloride, iodide and acetate; manganese bromide, chloride, and acetate, and mixtures thereof.

Suitable hydrogen halides (referred to herein as Group 7 co-catalysts) include HF, HCl, HBr and HI.

Preferred Group 7 co-catalysts include HI, HBr, and HCl.

Suitable halogenated hydrocarbons (referred to herein as Group 8 co-catalysts) are described in commonly assigned U.S. patent application Ser. No. 399,270, filed July 19, 1982, by R. Austin and and R. Michaelson, the disclosure of which is herein incorporated by reference including any halogenated hydrocarbon compound, e.g. wherein the hydrocarbyl portion is selected from saturated aliphatic, saturated alicyclic, aromatic and mixtures thereof.

More specifically, suitable Group 8 co-catalysts can be represented by the structural formula:

$$R'-(X)_{n''} \tag{IV}$$

wherein R' can be inertly substituted or unsubstituted: alkyl, typically alkyl of from about 1 to about 20, preferably from about 1 to about 10, most preferably from about 1 to about 5 carbons, aryl, typically aryl of from about 6 to about 14, preferably 6 to about 10, most preferably 6 carbons, aralkyl and alkaryl wherein the alkyl and aryl groups thereof are as defined immediately above, cycloalkyl, typically cycloalkyl of from about 4 to about 20, preferably from about 5 to about 15, and most preferably from about 5 to about 10 carbon atoms; X is at least one halogen independently selected from the group consisting of F, Cl, Br and I, and preferably I and Br; n'' is a number of from about 1 to about 10, preferably from about 1 to about 8 (e.g., 2 to 6), and most preferably from about 1 to about 6 (e.g., 2 to 4); and said R' substituents include hydroxy, ether and ester groups, said ether and ester substituents being as described in connection with $R_1$ of structural formula II. The term "inertly substituted" is defined herein to mean any organic or inorganic substituent which is stable under reaction conditions and does not adversely affect the performance of said co-catalyst, relative to the unsubstituted halogenated organic compound.

Representative examples of suitable Group 8 co-catalysts include iodomethane, bromomethane, iodoethane, bromoethane, 1,2-dibromoethane, 1-chloroethane, 1,2-dichloroethane, 1-iodopropane, 1-bromopropane, 1-chloropropane, 2-iodopropane, 2-bromopropane, 2-chloropropane, 1-iodobutane, 2-iodobutane, 2-bromobutane, 1-chlorobutane, 2-methyl-2-iodopropane, 2-methyl-2-bromopropane, 1-iodo-1,1-dimethylethane, 1bromo-1,1-dimethylethane, 1-chloro-1,1-dimethylethane, phenyliodomethane, phenylchloromethane, phenylbromomethane, 1,2-dichlorobenzene, 2-bromoethanol, 2-chloroethanol, 2-iodoethanol, 1-phenyl-2-iodoethane, 1-phenyl-4,4-dichlorobutane, 1-(1,2-dichloroethyl)benzene, 1-(1-chloropropyl) naphthalene and mixtures thereof.

Preferred Group 8 co-catalysts include iodomethane, bromomethane, 1-bromobutane, 1-iodobutane, 1-bromo-1,1-dimethylethane, 1-iodo-1,1-dimethylethane, 2-iodobutane, 2-bromobutane, 2-methyl-2-iodopropane, 2-methyl-2-bromopropane, 2-bromoethanol, 2-chloroethanol, 2-iodoethanol, and mixtures thereof.

The most preferred Group 8 co-catalyst contains iodine and include 1-iodobutane, iodomethane, 2-iodobutane, 2-methyl-2-iodopropane, 2-iodoethanol, and mixtures thereof.

Representative examples of suitable Group III-b, IV-b, V-b and VI-b metal halides (according to the periodic chart of Cotton and Wilkinson "Advanced Inorganic Chemistry" [3rd ed. 1972] referred to herein as Group 9 co-catalysts include halides of Al, Ga, In, Tl, Ge, Sn, Pb, P, Si, As, Sb, Bi, S, Se, Te, and Po.

Specific Group 9 metal halides include $AlCl_3$, $GaBr_3$, $TlCl_3$, $SiCl_4$, $SiBr_4$, $PI_3$, $PBr_3$, $SbF_5$, $SbBr_3$, $SbI_3$, $BiCl_3$, $BiBr_3$, $AsI_3$, $AsBr_3$, $AsCl_3$, $SeF_4$, $SeCl_4$, $SeBr_4$, $TeF_4$, and mixtures thereof.

Suitable halogen co-catalysts (referred to herein as Group 10 co-catalysts) include $F_2$, $Cl_2$, $Br_2$, and $I_2$.

Any of the co-catalysts described in each of the aforenoted Group 1 to 10 co-catalysts can be employed alone or in conjunction with one or more co-catalysts in the same group and/or with one or more of the co-catalysts in the remainder of said groups in any amounts effective to increase the rate and/or selectivity of the hydroxylation reaction relative to that observed in their absence.

Accordingly, while any effective amount of co-catalyst can be employed, it is contemplated that such effective amount constitute typically from about 0.1 to about 10,000 mole percent, preferably from about 0.50 to about 1,000 mole percent, and most preferably from about 10 to about 500 mole percent, based on the total number of moles of osmium in the osmium carbonyl catalyst employed.

Preferred combinations of co-catalysts include the use of at least one Group 1 co-catalyst in combination with at least one co-catalyst falling within any one or more co-catalyst Groups 2-9 (e.g., Group 6 or Group 8).

The most preferred catalysts are those of Group 1 and/or Group 8.

Illustrative examples of suitable co-catalyst combinations include $CuBr_2$ and NaCl; $CuCl_2$ and NaBr; $FeCl_3$ and NaCl; $CuBr_2$ and tetraethyl ammonium chloride; $FeCl_2$ and KBr; $FeBr_3$ and CsCl; CuI and NaBr; and n-butyl iodide and NaI.

The oxidant which is employed to oxidize the olefin is selected from the group consisting of organic hydroperoxides, hydrogen peroxide, and oxygen.

The preferred class of oxidants is the organohydroperoxides. Conventional organohydroperoxides include those having the formula:

$$R''OOH \tag{V}$$

wherein R'' is a substituted or unsubstituted alkyl, typically about $C_3$ to about $C_{20}$, preferably about $C_3$ to about $C_{10}$, most preferably about $C_3$ to about $C_6$ alkyl; aryl, typically $C_6$ to $C_{14}$, preferably $C_6$ to $C_{10}$, most preferably $C_6$ aryl; aralkyl and alkaryl wherein the aryl and alkyl groups thereof are as defined immediately above; cycloalkyl, typically about $C_4$ to about $C_{20}$, preferably about $C_4$ to about $C_{10}$, most preferably about $C_4$ to about $C_8$ cycloalkyl; as well as oxacyclic having 1 to about 5 oxygens and preferably 3 to about 20 carbons, and azacyclic having 1 to about 5 nitrogens and preferably about 3 to about 20 carbons; and wherein the substitutents of said R'' group include halogen, hydroxyl, ester and ether groups.

Representative examples of suitable organohydroperoxides include ethylbenzyl hydroperoxide, t-butyl hydroperoxide, t-amyl hydroperoxide, cumene hydroperoxide, methyl-2-hydroperoxy-2-methyl propionate, 2-methyl-2-hydroperoxy propanoic acid, pyrrolehydroperoxide, furan hydroperoxide, 2-butylhydroperoxide, cyclohexyl hydroperoxide, and 1-phenylethylhydroperoxide.

The most preferred organic hydroperoxides include t-butyl hydroperoxide, ethylbenzenehydroperoxide, and t-amyl hydroperoxide. Frequently these hydroperoxides are made by the molecular oxygen oxidation of the corresponding hydrocarbon which also produces an alcohol as a by-product. For example, when isobutane is oxidized with molecular oxygen there is produced tertiary butyl hydroperoxide and tertiary butyl alcohol. It is not necessary to separate the alcohol from the hydroperoxide since the alcohol can function as a diluent or solvent.

The amount of organohydroperoxide employed is not critical and can vary widely. Generally, the organohydroperoxide is employed in less than stoichiometric requirements (i.e., less than 1:1 molar ratio of organohydroperoxide per mole of ethylenic unsaturation in the olefin to be hydroxylated. Thus, while any amount of hydroperoxide effective to hydroxylate the olefin can be employed, it is contemplated that such effective amount constitute a ratio of moles of ethylenic unsaturation in the olefin to moles or organohydroperoxide of from about 0.5:1 to about 100:1, preferably from about 1:1 to about 20:1 and most preferably from about 2:1 to about 10:1.

While the organohydroperoxide can be added to the reaction mixture in anhydrous form, it may also be added as an aqueous solution comprising from about 1 to about 99%, preferably from about 10 to about 90%, and most preferably from about 20 to about 70%, by weight hydroperoxide, based on the weight of the aqueous hydroperoxide solution.

A suitable alternative oxidant is $H_2O_2$. The amount of $H_2O_2$ employed can vary over wide limits and can be any effective amount. Accordingly, effective molar ratios of olefin ethylenic unsaturation to $H_2O_2$ can vary from about 0.5:1 to about 100:1, preferably from about 1:1 to about 20:1, most preferably from about 2:1 to about 10:1. The $H_2O_2$ can be employed in anhydrous form or as an aqueous solution. Such aqueous solutions typically will contain from about 3 to about 99.9%, preferably from about 20 to about 75%, and most preferably from about 20 to about 45% (e.g., 25 to 35%), by weight $H_2O_2$ based on the total weight of the aqueous solution.

A further alternative oxidant is oxygen or an oxygen containing gaseous mixture such as air. If oxygen is employed as the oxidant, it is preferred to also employ at least one Group 6 co-catalyst (described above) in conjunction therewith.

The molar ratio of oxygen to olefin ethylenic unsaturation also can vary widely but for safety reasons it is maintained outside explosive limits, said explosive limits usually being expressed as weight percent ratios.

For example, when hydroxylating ethylene or propylene, if oxygen is in excess, the ratio typically will be about 98 weight percent oxygen or more and 2 percent or less of the olefin based on the total weight of these two reactants. Alternatively, if the olefin is in large excess, the oxygen concentration typically will be about 10 weight percent and about 90 weight percent olefin.

When oxygen is in excess, olefin can be added during the reaction as the reaction proceeds. On the other hand, where the olefin is in excess, oxygen can be added during the reaction as the oxygen is consumed.

It is also critical to have water present during the hydroxylation reaction since the water is believed to contribute one of the oxygen molecules constituting one of the hydroxyl groups in the resulting glycol. The source of this water is not critical. Thus, the water formed in-situ during the reaction between $H_2O_2$ and olefin can contribute to the water content for the reaction. Water can also be added separately, preferably as the solvent for the organohydroperoxide. Consequently, water is provided to, and/or is present in at least a stoichiometric molar ratio with the molar amount of ethylenic unsaturation of the olefin to be hydroxylated. Such ratios preferably also are present in the reaction mixture at any given time after start-up. Accordingly, water is present in the reaction mixture at molar ratios of water to olefin ethylenic unsaturation to be hydroxylated in the reaction mixture of from about 1:1 to about 100:1, preferably from about 1:1 to about 50:1, and most preferably from about 1:1 to about 20:1. Such molar ratios typically can be achieved by controlling the amount of water in the reaction mixture to be from about 1 to about 90 percent, preferably from about 15 to about 85 percent, and most preferably from about 20 to about 60 percent, by weight, based on the total weight of the reaction mixture. Preferably the amount of water employed is less than that which will cause separation of the reaction mixture into an aqueous phase and organic phase although this is not a critical condition.

Olefins which can be hydroxylated in accordance with the present invention contain at least one ethylenic unsaturation and comprise any of the unsaturated aliphatic or alicyclic compounds well known in the art for undergoing such hydroxylation reactions. Typically, such compounds will contain from about 2 to about 20 carbons, preferably from about 2 to about 10 carbons, and most preferably from about 2 to about 5 carbons. Such compounds may be straight or branched chain, mono-olefinic, di-olefinic, or polyolefinic, conjugated or non-conjugated. They may be substituted with such groups as aryl, preferably aryl of from 6 to about 14 carbons, alkyl, preferably alkyl of from 1 to 10 carbons, or aralkyl and alkaryl wherein the alkyl and aryl portions thereof are as described above, as well as with functional groups such as hydroxy, carboxyl and anhydride.

Typical of such olefins are those represented by the structural formula:

(VI)

wherein $R_6$, $R_7$, $R_8$, and $R_9$, which may be the same or different, are selected from the group consisting of hydrogen; substituted or unsubstituted: alkyl, aryl, alkaryl, and aralkyl hydrocarbyl groups, said hydrocarbyl groups being preferably as defined immediately above; or any two or said $R_{7-9}$ groups together can constitute a cycloalkyl group typically of from about 4 to about 12, preferably from about 5 to about 8 carbons.

Representative olefins which can be hydroxylated and contain at least one ethylenic unsaturation include: ethylene, propylene, butene-1, butene-2, isobutene, butadiene, pentene-1, pentene-2, hexene, isohexene, heptene, 3-methylhexene, octene-1, isooctene, nonene, decene, dodecene, tridecene, pentadecene, octadecene, eicosene, docosene, tricosene, tetracosene, pentacosene, butadiene, pentadiene, hexadiene, octadiene, decadiene, tridecadiene, eicosadiene, tetracosadiene, cyclopentene, cyclohexene, cycloheptene, methylcyclohexene, isopropylcyclohexene, butylcyclohexene, octylcyclohexene, dodecylcyclohexene, acrolein, acrylic acid, 1,2,3,4-tetrahydrophthalic anhydride, methyl methacrylate, styrene, cholesterol and mixtures thereof.

The preferred olefins are ethylene, propylene, isobutylene, butadiene, styrene, allyl alcohol and allyl chloride.

The most preferred olefins are ethylene and propylene.

The preferred mode for conducting the hydroxylation reaction is contact the unsupported osmium carbonyl catalyst with a liquid reaction mixture, preferably provided as a homogeneous or substantially homogeneous medium and preferably but optionally by using an inert organic solvent to dissolve or assist in dissolving the co-catalysts and reactants.

Partial immiscibility of the solvent with water is acceptable although not preferred. By an inert solvent is meant one which does not undergo oxidation during the course of the reaction.

Suitable inert organic solvents preferably possess polar functional groups and include aliphatic or aromatic alcohols having from 1 to about 10 carbon atoms, preferably tertiary alcohols, aliphatic or aromatic ketones having from 3 to about 10 carbons atoms, aliphatic or alicyclic ethers having from 2 to about 10 carbon atoms, glycols having from 2 to about 10 carbon atoms, N,N-dialkyl amides having from 3 to about 10 carbon atoms, nitriles having from about 2 to about 10 carbons, aliphatic or aromatic sulfoxides having from 2 to about 14 carbon atoms, aliphatic or aromatic sulfones having from 2 to about 14 carbon atoms, and the like. Examples of suitable solvents include methanol, ethanol, propanol, butanol, hexanol, decanol, t-butyl alcohol, t-amyl alcohol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide, dimethyl sulfone, diethyl sulfone, tetra methylene sulfone, diphenyl sulfone, acetonitrile, pyridine, dioxane, tetra hydrofuran, tetra hydropyran, dioxolane, and mixtures thereof.

The preferred solvents include those which are substantially or completely miscible with water such as t-butyl alcohol, methanol, and acetonitrile.

The most preferred solvent(s) is the product alcohol derived from the organic hydroperoxide or mixtures of the product glycol and the organohydroperoxide derived product alcohol.

For example, when ethylene is hydroxylated using t-butyl hydroperoxide, the preferred solvent is t-butyl alcohol or a mixture of ethylene glycol and t-butyl alcohol, the latter being formed in-situ from t-butyl hydroperoxide.

The inert solvent is preferably employed in amounts sufficient to achieve a homogeneous solution with respect to at least the olefin and oxidant. Typically such amounts can vary from about 0 to about 90 percent, preferably from about 20 to about 80 percent, and most preferably from about 20 to about 50 percent, by weight, based on the total weight of the reaction mixture.

The pH of the reaction mixture during the hydroxylation reaction need not be rigidly controlled although it will typically not be allowed to drop below about 4, preferably not below about 6. Likewise, the pH of the reaction mixture typically will not be allowed to exceed about 12 although the process can still be conducted at a pH below 4 and above 12. Accordingly, the pH of the reaction mixture typically will be maintained between 4 and 12, preferably between about 5 and about 12, and most preferably between about 6 and about 12. The pH of the reaction mixture can be controlled by the use of conventional buffers or base where needed. Preferably, pH control is achieved by the use of co-catalyst base or other suitable basic material such as pyridine or a buffer.

While the osmium carbonyl catalysts may be employed in supported form as described and claimed in commonly assigned U.S. patent application Ser. No. 397,997, filed July 14, 1982, the disclosure of which is herein incorporated by reference, the hydroxylation reaction of the present invention is conducted in a homogeneous solution of reactants and osmium carbonyl catalyst.

Accordingly, in carrying out a preferred embodiment of the invention, olefin, water, oxidant, osmium carbonyl catalyst, optional co-catalyst, and optional inert solvent are contacted by admixing to form a liquid reaction mixture in a manner and under conditions sufficient to hydroxylate the olefin, i.e., to convert at least one of the ethylenic unsaturations possessed thereby to its corresponding diol. The manner and order of addition of each of the individual components of the liquid reaction mixture to the reaction vessel is not critical. However, when an organohydroperoxide is used as the oxidant, it is preferred to mix the osmium carbonyl catalyst, and optional co-catalyst if employed, with an aqueous solution containing solvent, additional additives such as buffers, where needed, olefin, and finally organic hydroperoxide.

Accordingly, the initial typical reaction medium exclusive of olefin when using an organohydroperoxide oxidant will typically comprise: (a) an organohydroperoxide in an amount of from about 1 to 70 percent, preferably from about 5 to about 60 percent, and most preferably from about 10 to about 50 percent, by weight, based on the weight of the reaction medium exclusive of the weight of olefin, catalyst, and any other additive (e.g. buffers) and/or co-catalysts if present; (b) osmium carbonyl catalyst in amounts heretofore specified; (c) water subject, to the molar constraints heretofore specified, in an amount of from about 1 to about 98 percent, preferably from about 10 to about 80 percent, and most preferably from about 30 to about 60 percent, by weight, based on the total weight of the reaction medium exclusive of the weight of olefin, catalyst, and any other additives (e.g. buffers) and/or co-catalysts if present; and (d) inert organic solvent in an amount of from about 0 to about 99 percent, preferably from about 20 to about 80 percent, and most preferably from about 30 to about 60 percent, by weight, based on the weight of the reaction mixture exclusive of the weight of olefin, catalyst other additives, and/or co-catalyst if present. Co-catalyst if employed is used in effective amounts as described above as are pH control additives where desired.

When an aqueous $H_2O_2$ solution (as defined above) is employed as the oxidant, it preferably will comprise from about 1 to about 70 percent, preferably from about 5 to about 60 percent, and most preferably from about 10 to about 50 percent, by weight, based on the weight of the reaction mixture exclusive of olefin, catalyst, other additives, and/or co-catalyst if present.

For the production of ethylene glycol, propylene glycol or any product derived from any unsaturated gaseous olefin, the latter may be bubbled through the reaction mixture containing the components described herein or it may be introduced under pressure. Likewise with the oxygen-containing gas if employed as the oxidant. However, it is preferred that the reaction takes place in the liquid phase. Consequently, sufficient pressure is preferably employed to maintain the gaseous reactants in the liquid phase. Otherwise, the reaction pressure is not critical and can be atmospheric, sub-atmospheric, or super-atmospheric.

When the olefin reactant is a liquid or is dissolved in the reaction mixture under pressure, its concentration in the reaction mixture typically will vary from about 1 to about 98 percent, preferably from about 10 to about 80 percent, and most preferably from about 30 to about 60 percent, by weight, based on the total weight of the reactant mixture inclusive of the weight of components (a) through (d) described above.

The hydroxylation reaction is typically conducted at temperatures which can vary over wide limits although it is preferred to maintain the reaction mixture in the liquid phase. Accordingly, typical reaction temperatures can vary from about 0° to about 250° C., preferably from about 20° to about 150° C., and most preferably from about 20° to about 130° C.

At temperatures greater than the aforenoted ranges, the reaction rate may increase substantially but this usually occurs at the expense of a significant reduction in selectivity. At very low reaction temperatures, e.g., below about 0° C. the reaction rate decreases to a commercially undesirable degree. Accordingly, while the reaction temperature is not critical and can vary over a wide range, one normally would not operate at temperature extremes outside the aforenoted ranges.

The hydroxylation reaction can be performed as a batch reaction, as a continuous reaction or as a semicontinous reaction.

In the batch reaction, a reaction mixture containing the above described components is charged into the reaction vessel along with olefin if in liquid form. Alternatively, the reaction vessel is then pressurized with olefin if in gaseous form and oxygen if employed. It may be desirable to heat the liquid reaction mixture to reaction temperature prior to pressurizing with the reactant gases. The reaction is allowed to proceed to completion, typically for a period of from about 0.05 to about 5 hours, preferably from about 0.5 to about 3 hours, and most preferably from about 0.5 to about 2 hours.

In the continuous process, the components can be introduced into the inlet of an elongated reactor at a rate such that substantially complete reaction will have taken place by the time the reaction mixture reaches the reactor outlet. The reaction can be carried out in a semicontinuous manner by metering the reactant mixture components into a series of two or more tank reactors at the appropriate rate to maintain the reactor liquid level.

Additionally, the process may be run in either of the aforementioned modes by altering the reaction conditions and/or, the reactant, solvent, catalyst, co-catalyst, and pH control additive concentrations during the course of the reaction. Thus, the process may be run by changing the temperature, pressure, catalyst concentration, oxidant concentration, and/or olefin concentration.

The spent reaction mixture after removal of unreacted olefin is a solution of product glycol, by-products if any, solvent, water, catalyst and optional co-catalyst. The volatile components are distilled out of the reaction mixture into various fractions leaving non-volatile catalyst components in the still. The product glycol is then separated from the high boiling distillate.

The following examples are given as specific illustrations of the claimed invention. It should be understood, however, that the invention is not limited to the specific details set forth in the examples. All parts and percentages in the examples as well as in the remainder of the specification are by weight unless otherwise specified. Furthermore, and unless otherwise specified, while the following examples may be written in the present tense, they represent work actually performed.

Unless otherwise specified, in the following examples selectivity, conversion and yield are calculated as follows:

$$\% \text{ selectivity} = \frac{\text{moles of glycol formed}}{\text{moles of oxidant consumed}} \times 100$$

$$\% \text{ conversion} = \frac{\text{moles of oxidant consumed}}{\text{moles of oxidant charged}} \times 100$$

$$\% \text{ yield} = \frac{\% \text{ conversion} \times \% \text{ selectivity}}{100}$$

EXAMPLE 1

Into a 100 ml 3-neck round bottom flask equipped with a magnetic stirrer, reflux condenser, dropping funnel, and thermometer, is charged $Os_3(CO)_{12}$ (0.011 mmole), t-butyl alcohol 10.0 g, 1-octene 3.0 g (15 mmole) and $H_2O$ 3.0 g. While stirring the contents of the flask, 0.5 mmole of NaI co-catalyst is then added, followed by the dropwise addition of 1.9 g of an aqueous solution containing 70% by weight thereof t-butyl hydroperoxide at ambient temperature (25° C.) over a period of about 10 min. After 45 min. of continuous agitation measured from the completion of the hydroperoxide addition, the solution is analyzed by gas chromatography. Complete conversion of the hydroperoxide is obtained and the selectivity to glycol (1,2-octanediol) is 90%.

EXAMPLE 2

Example 1 is repeated with the exception that the NaI co-catalyst is omitted. The hydroperoxide conversion is 20% and the selectivity to 1,2-octanediol is 90%.

EXAMPLE 3

Example 1 is repeated with the exception that the NaI co-catalyst is replaced with 1.0 mmole of $CH_3I$ and 1.0 mmole of NaOH as the co-catalysts. Conversion is 100% and selectivity to 1,2-octanediol is 70% with about 16% selectivity to ketol.

EXAMPLES 4 TO 6

The quantities of materials shown in Table 1 for each of Examples 4 to 6 are charged to one of three glass bottles, each containing a magnetic stirring bar. The bottles are capped and the contents stirred at room temperature for about 18 hours. The caps are removed and stirring continued until the excess isobutene had evaporated. Tetraglyme (1.11 g) is added to each bottle and the solutions analyzed by gas liquid chromatography, which shows the formation of the quantities of isobutylene glycol indicated in Table 1. The NaOH is added as a 0.8 wt. % solution in water and the NaI is added as a 3 wt. % solution thereof in water.

TABLE 1

| Example No. | 4 | 5 | 6 |
| --- | --- | --- | --- |
| Co-catalyst (g) | NaOH(0.49) | NaOH(0.52) | NaI(0.49) |
| (a)90% t-BuOOH (g) | 10.00 | 1.00 | 1.00 |
| t-BuOH (g) | 1.29 | 13.44 | 13.42 |
| $H_2O$ (g) | 6.22 | 3.05 | 3.06 |
| (b)isobutene sol. (g) | 42.00 | 42.00 | 42.00 |
| $Os_3(CO)_{12}$ (g) | 0.006 | 0.006 | 0.006 |
| Conversion (%) | 100 | 100 | 100 |
| Selectivity (%) | 23 | 75 | 97 |
| Yield (%) | 23 | 75 | 97 |

(a)90% t-BuOOH = a 90% by weight solution of t-butyl hydroperoxide dissolved in a 1:1 (w/w) solution of t-butyl alcohol and water.
(b)Isobutene sol. = an aqueous solution comprising 20% by weight, isobutene, and 70% by weight, t-butyl alcohol, with the remainder being water.

EXAMPLE 7

The following example illustrates the use of an osmium carbonyl catalyst and an oxygen oxidant.

Into a 300 ml titanium autoclave is charged at room temperature (25° C.) 49.8 g propylene, 0.09 g $Os_3(CO)_{12}$, 20.0 g $CH_3CN$ (solvent), 70.0 g $H_2O$, and 1.10 g $CuBr_2$ (co-catalyst). After warming the mixture to 100° C., oxygen (80 psig) is added slowly to produce a total pressure of 700 psig. The reaction mixture is stirred at 100° C. for 2.0 hours and then cooled to room temperature. The pH of the reaction mixture at the end of the run is about 4.0. The selectivity to propylene glycol is 99% at a conversion of about 25.2%, 1.0 g of propylene glycol being produced. The low conversion observed is believed to be due to the low degree of solubilization of the propylene in the reaction mixture. However, selectivity is extremely good in the presence of the osmium carbonyl catalyst and co-catalyst.

EXAMPLE 8

The following example illustrates the use of an osmium carbonyl catalyst and hydrogen peroxide as the oxidant.

Accordingly, Example 1 is repeated with the exception that hydrogen peroxide (20.0 mmol), charged as a 30% aqueous solution thereof, is used in place of t-butyl hydroperoxide as the oxidant. The selectivity to 1,2-octanediol is 99% and the yield based on $H_2O_2$ charged is 15.5%.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for hydroxylating olefins which comprises reacting in admixture water, at least one olefinic compound having at least one ethylenic unsaturation, and an oxidant selected from the group consisting of organic hydroperoxide, $H_2O_2$ and oxygen in the presence of a catalyst composition in a manner and under conditions sufficient to hydroxylate at least one of said ethylenically unsaturated groups, said catalyst compositions (a) being capable of catalyzing said hydroxylation reaction and (b) comprising, as initially added to said admixture, at least one unsupported osmium carbonyl compound and optionally at least one co-catalyst.

2. The process of claim 1 wherein the osmium carbonyl compound is selected from the group consisting of $Os(CO)_5$, $Os_2(CO)_9$, $Os_3(CO)_{12}$, $Os_5(CO)_{16}$, $Os_6(CO)_{18}$, $Os_7(CO)_{21}$, and $Os_8(CO)_{23}$.

3. The process of claim 2 wherein the osmium carbonyl compound is $Os_3(CO)_{12}$.

4. The process of claim 1 wherein the osmium carbonyl compound is at least one osmium complex represented by the structural formulae selected from the group consisting of: $[Os(CO)X_5]^{-2}$, $[Os(CO)_2X_4]^{-2}$, $[Os(CO)_3X_3]^{-1}$, and $[Os(CO)_4X]^{-2}$, wherein X is halide.

5. The process of claim 4 wherein X is selected from the group consisting of chlorine, bromine and iodine.

6. The process of claim 1 wherein the osmium carbonyl compound is at least one osmium complex represented by the structural formula: $Os(X'')_a(CO)_b(Y)_c(PR_3)_d$ wherein $X''$ is independently selected from the group consisting of hydrogen, cyclopentadienyl, and halogen, Y is independently selected from NO, $NH_3$, and $N_2$, R is a hydrocarbyl group independently selected from the groupd consisting of alkyl, aryl, alkaryl, and aralkyl, "a" and "c" represent numbers of from 0 to 3, "b" represents a number of at least 1, "d" represents a number of 2 or 3 and the sum of a, b, c, and d is selected in conjunction with the valence of osmium to achieve a neutral complex.

7. The process of claim 1 wherein the oxidant is at least one organic hydroperoxide.

8. The process of claim 7 wherein the organic hydroperoxide is selected from the group consisting of t-butyl hydroperoxide, ethylbenzene hydroperoxide, t-amyl hydroperoxide and 2-butyl hydroperoxide.

9. The process of claim 1 wherein the oxidant is hydrogen peroxide.

10. The process of claim 1 wherein the oxidant is oxygen.

11. The process of claim 1 wherein the oxidant is oxygen and said catalyst composition comprises at least one transition metal co-catalyst selected from the group consisting of transition metal: halide, porphyrin, pseudohalide, carboxylate and aryloate, said transition metal being selected from the group consisting of Fe, Co, Ni, Cu, V, Cr, Mn, Sc, Ti, Mo, Ru, Rh, Pd and W.

12. The process of claim 1 wherein the oxidant is selected from the group consisting of organic hydroperoxides and $H_2O_2$, and the catalyst composition comprises at least one co-catalyst selected from the group consisting of alkali metal halide, and alkaline earth metal halide.

13. The process of claim 1 wherein the olefin is selected from the group consisting of ethylene, propylene, and mixtures thereof.

14. The process of claim 1 wherein said hydroxylation reaction is conducted in the presence of an inert solvent.

15. The process of claim 14 wherein the oxidant is t-butyl hydroperoxide, the olefin is selected from the group consisting of ethylene, propylene, and mixtures, and the inert solvent is selected from the group consisting of t-butyl alcohol, ethylene glycol, propylene glycol and mixtures thereof.

* * * * *